United States Patent
Celentano et al.

(10) Patent No.: US 8,394,246 B2
(45) Date of Patent: Mar. 12, 2013

(54) SYSTEM AND METHOD FOR THE ELECTROCHEMICAL MEASUREMENT OF AN ANALYTE EMPLOYING A REMOTE SENSOR

(75) Inventors: Michael J. Celentano, Indianapolis, IN (US); P. Douglas Walling, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 868 days.

(21) Appl. No.: 12/534,177

(22) Filed: Aug. 3, 2009

(65) Prior Publication Data
US 2010/0213080 A1 Aug. 26, 2010

Related U.S. Application Data (63) Continuation of application No. 12/390,532, filed on Feb. 23, 2009, now abandoned.

(51) Int. Cl.
G01N 27/327 (2006.01)
G01N 27/416 (2006.01)

(52) U.S. Cl. ............ 204/403.02; 204/403.04; 422/82.01

(58) Field of Classification Search .......... 204/403.01–403.15; 205/777.5, 205/778, 792; 422/82.01–82.03
See application file for complete search history.

(56) References Cited

U.S. PATENT DOCUMENTS

| | | | |
|---|---|---|---|
| 5,101,814 A | 4/1992 | Palti | |
| 6,217,744 B1 | 4/2001 | Crosby | |
| 6,285,899 B1 | 9/2001 | Ghaem et al. | |
| 6,641,533 B2 | 11/2003 | Causey, III et al. | |
| 7,125,382 B2 | 10/2006 | Zhou et al. | |
| 7,297,112 B2 | 11/2007 | Zhou et al. | |
| 7,382,258 B2 | 6/2008 | Oldham et al. | |
| 8,099,074 B2 * | 1/2012 | Ebner et al. | 455/343.3 |
| 2006/0217599 A1 | 9/2006 | Ohta et al. | |
| 2006/0226985 A1 | 10/2006 | Goodnow et al. | |
| 2006/0290496 A1 | 12/2006 | Peeters | |
| 2007/0231846 A1 | 10/2007 | Cosentino et al. | |
| 2007/0237678 A1 | 10/2007 | Roesicke et al. | |
| 2007/0270672 A1 | 11/2007 | Hayter | |
| 2008/0145277 A1 | 6/2008 | Wohland | |
| 2008/0162054 A1 | 7/2008 | Tam | |

(Continued)

FOREIGN PATENT DOCUMENTS

| EP | 1956525 A2 | 8/2008 |
|---|---|---|
| EP | 2 098 863 A1 | 9/2009 |

(Continued)

OTHER PUBLICATIONS

International Patent Application PCT/EP2010/001075, International Preliminary Report on Patentability, Aug. 23, 2011.

(Continued)

Primary Examiner — Alex Noguerola
(74) Attorney, Agent, or Firm — Krieg DeVault LLP (57) ABSTRACT

A remote measurement system measures the concentrations of analytes in fluid samples. The system includes a metering device that can receive signals from a test strip or alternatively interrogate the test strip to obtain information. The test strip includes an area for receiving a fluid sample and electrochemically producing a current response that is sensed within the fluid sample. The test strip also includes an antenna and a radio frequency signal circuit for transmitting a signal indicative of the current response of a fluid sample to be analyzed. The metering device receives the signal and can convert it into a readable display in some embodiments. Remote electrochemical analysis of a fluid sample is thereby obtained.

21 Claims, 3 Drawing Sheets

U.S. PATENT DOCUMENTS

| | | |
|---|---|---|
| 2008/0194934 A1* | 8/2008 | Ray et al. ............ 600/347 |
| 2008/0294024 A1 | 11/2008 | Cosentino et al. |
| 2009/0022630 A1 | 1/2009 | Hoenes et al. |

FOREIGN PATENT DOCUMENTS

| | | |
|---|---|---|
| JP | 2008229269 A | 10/2008 |
| WO | WO 2005/040793 A1 | 5/2005 |
| WO | WO 2006/026741 A1 | 3/2006 |
| WO | WO 2006/040106 A1 | 4/2006 |
| WO | WO 2006/086423 A2 | 8/2006 |
| WO | WO 2008/072275 A2 | 6/2008 |

OTHER PUBLICATIONS

International Patent Application No. PCT/EP2010/001075, International Search Report and Written Opinion, May 21, 2010, 12 pages.

* cited by examiner

SYSTEM AND METHOD FOR THE ELECTROCHEMICAL MEASUREMENT OF AN ANALYTE EMPLOYING A REMOTE SENSOR

CROSS REFERENCE

This application is a continuation of and claims the benefit of U.S. application Ser. No. 12/390,532 filed Feb. 23, 2009 now abandoned.

TECHNICAL FIELD

The present invention relates to a measurement method and apparatus for use in measuring concentrations of an analyte in a fluid. The invention relates more particularly, but not exclusively, to a method and apparatus which may be used for remotely measuring the concentration of glucose in blood.

BACKGROUND

Measuring the concentration of substances, particularly in the presence of other, confounding substances, is important in many fields, and especially in medical diagnosis. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for measuring the concentration of analytes in a blood sample, such as, for example, glucose. Such methods typically fall into one of two categories: optical methods and electrochemical methods. Optical methods generally involve spectroscopy to observe the spectrum shift in the fluid caused by concentration of the analyte, typically in conjunction with a reagent that produces a known color when combined with the analyte. Electrochemical methods generally rely upon the correlation between the current response of a blood sample and the concentration of the analyte, typically in conjunction with a reagent that produces charge-carriers when combined with the analyte. See, for example, U.S. Pat. No. 4,919,770 to Preidel, et al., and U.S. Pat. No. 6,054,039 to Shieh, which are hereby incorporated in their entireties.

Optical systems have rapidly lost popularity to the electrochemical systems, largely due to the fact that the blood sample must be inserted into the meter itself (into the internal optics block), thereby coming into direct contact with the meter itself. This required a thorough cleaning of the meter internal and external surfaces between uses, in order to prevent contamination of a subsequent sample and to allow a single meter to be safely used on multiple patients in a hospital setting or in a doctor's office without undue bio-risk. In electrochemical devices, the sample chamber is typically placed in a disposable test strip, which is inserted at one end into the meter. This way, the blood sample never makes contact with the meter.

An important confounding variable in electrochemical blood glucose testing is the change in the concentration of the reaction product over time. For example, in strips employing a dry reagent, initially, the reagent on the strip reacts at an accelerating pace, as it becomes wetted. Subsequently, the pace of reaction drops off, as the concentration of the blood glucose in the neighborhood of the reagent drops due to reaction. The concentration of the product in the neighborhood of the reagent initially increases as it is generated by the reaction, but if the reagent is exhausted, will subsequently decrease, as the product diffuses into the rest of the sample. In some prior art systems, the time variation is accounted for by letting the reaction run to completion. However, this method is undesirable because it is very slow. More recent systems have dealt with the time variation by calibrating the measurement to the period between contact of the sample with the reagent and the point of measurement.

However, this method poses a different problem, since it requires that the test strip be inserted into the meter before it is dosed. As a consequence, it requires far more dexterity to successfully dose the strip in such systems, since the meter and strip together are far larger and more cumbersome than the strip by itself. This is especially problematic since diabetics, who are the primary users of blood glucose measuring systems, often suffer from a loss of both fine and coarse motor control. It is well-established in the field of ergonomics that fine motor control (dexterity) is best achieved while attempting to capture a small droplet of blood, derived from penetration of the patient's skin, when a small device such as a test strip is used, in contrast to the combination of the much larger test meter with a test strip inserted therein. In the professional setting (bedside testing), the professional conducting the test often lacks a stable work surface as an aid while conducting the test procedure. In such cases, bringing a large apparatus into contact with a small droplet of blood without the aid of a stable surface is challenging.

Thus, a system and method are needed that accurately measure blood glucose, using a test strip which does not need to be inserted into the meter prior to dosing, and a meter that does not require direct contact with the sample to make the measurement. The present invention is directed to this need, among others.

SUMMARY

One embodiment of the present invention is a system comprising a remote metering device for receiving an impedance change signal and a sensing device constructed and arranged to receive a fluid sample to be analyzed comprising: at least one electrode operatively coupled to said fluid sample for electrochemically sensing an impedance change in said fluid sample; and an antenna operatively coupled to said at least one electrode constructed and arranged to transmit a signal indicative of the impedance change.

Another embodiment of the present invention includes a method comprising the steps of activating a test strip having a thin film battery; obtaining a fluid sample; applying said fluid sample to said test strip; determining sample presence using said test strip; measuring the concentration of an analyte in said sample; interrogating said test strip using a metering device; transmitting information concerning the measurement of the concentration of said analyte from said test strip to said metering device.

BRIEF DESCRIPTION OF THE DRAWINGS

Although the characteristic features of this invention will be particularly pointed out in the claims, the invention itself.

DETAILED DESCRIPTION OF SELECTED EMBODIMENTS

For the purposes of promoting an understanding of the principles of the invention, reference will now be made to selected embodiments and specific language will be used to describe the same. It will nevertheless be understood that no limitation of the scope of the invention is thereby intended. Such alternations and further modifications in the invention, and such further applications of the principles of the invention as described herein as would normally occur to one skilled in the art to which the invention pertains, are contemplated, and desired to be protected.

One embodiment of a blood glucose testing system disclosed provides a convenient and fast way to test blood glucose using test strips that can be dosed without having to be inserted into a metering device. The test strips are therefore very easy to handle and the blood sample does not have to be subsequently brought into contact with the meter. Thus, the robustness of the meter is enhanced because it stays clean, avoids contamination of subsequent samples, and without a test strip port it can be designed to be sealed to outside contaminants such as dirt and moisture that may otherwise affect a measurement result. As used herein, the terms "test strip" and "strip" are intended to cover any physical configuration of a biosensor, and are not limited to longitudinally extending strips as are commonly found in the prior art. Therefore, "test strip" and "strip," as used herein, includes biosensors having rectangular, square, circular, triangular, trapezoidal, polyhedral, spherical or any other desired shape.

The disclosed embodiments are non-limiting examples of sensing devices that measure or detect the presence of at least one analyte of interest. Illustratively, the disclosed embodiments employ test strips that remotely measure blood glucose. In some embodiments, the measurement data collected by the test strips is returned to the meter by modulating an antenna, which creates a varying disturbance in the electromagnetic field generated by the meter. Thus, most of the power, if not all of the power, for the transmission is supplied by the meter, rather than the test strip, so that the strip can be powered by a very small and inexpensive power source, such as a thin-film battery or even no battery at all. Since the test strips are disposable, this cost savings is extremely valuable to the patient in the long run. An additional beneficial feature of this remote data transfer arrangement is the ability of the system to automatically download calibration information from the test strip. It will be appreciated that other similar information may be encoded into a carrier wave signal and sent or received by the meter and test strip. As a non-limiting example, the information related to the test strip manufacture information including, but not limited to, batch calibration data, date codes, expiration dates, manufacture specific data, manufacture validation information, test meter compatibility profile, and test strip type. Likewise, the carrier wave signal can be encoded to include control messages. Illustrative control messages may include test strip activation signals, meter activation signals, error conditions, or dosage sufficiency indication. In yet another non-limiting example, the carrier wave is encoded to communicate test related date and/or information including Cottrell current measurements, Cottrell Failsafe Ratio measurement, dosage sufficiency data, and analyte detection measurement data.

Figure 1:
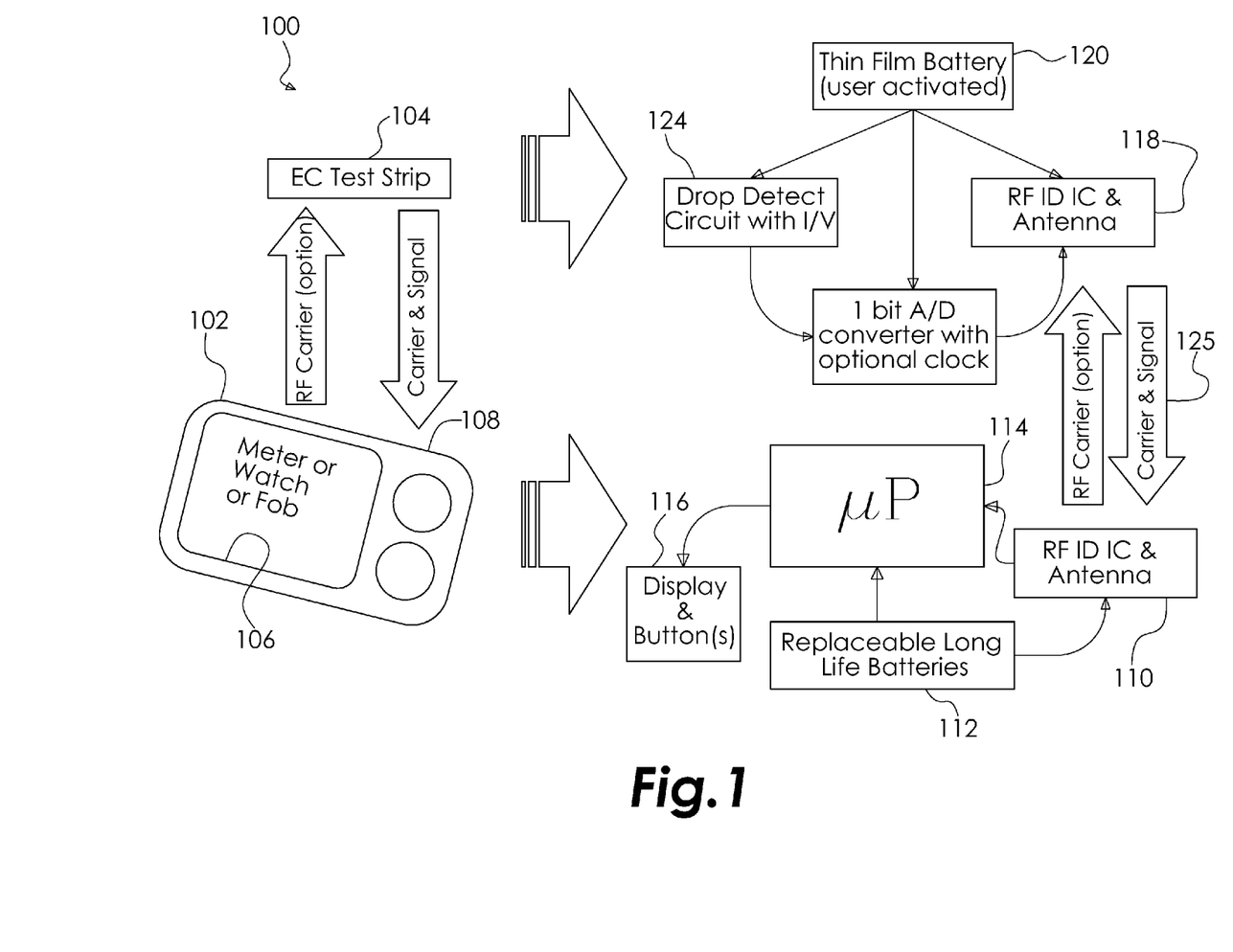
FIG. 1 is a schematic illustration of a metering device and test strip system according to one embodiment.

Referring now to the drawings, FIG. 1 illustrates a remote measurement system 100 according to one embodiment. The remote measuring system 100 generally comprises a metering device 102 and a test strip 104. The metering device 102 receives a signal from the test strip 104 indicative of the concentration of an analyte in the blood or fluid sample present on the test strip 104. In addition, the metering device 102 receives information about the quantity and quality of the fluid sample that is being analyzed in some embodiments. These aspects of the fluid sample may be determined first before the analyte is measured.

The metering device 102 can be a simple device having a display screen 106 and buttons 108 as illustrated in FIG. 1. Alternatively, it can have additional levels of complexity in other embodiments. The display screen 106 in some embodiments is a liquid crystal display screen. The display screen 106 is formed to display numbers and/or letters that represent the concentration of an analyte in the fluid sample. In some embodiments, the meter 102 is contained within a sealed housing having no openings therein (i.e. any opening in the meter "case" is filled with a display screen, button, or other component such that the meter housing is effectively sealed and can even be designed to be waterproof). Alternatively, in other embodiments, the metering device 102 has a different configuration. For one example, in some embodiments the metering device 102 is a watch. The watch may be a stand-alone device or it may be part of a personal area network (PAN) in combination with other personal specific devices. A personal area network generally refers to the combination of two or more person specific electronic devices having a symbiotic relationship located directly within the close personal space of the person. Moreover, other types of metering devices 102 readily apparent to those skilled in the art are also contemplated for alternate embodiments.

The test strip 104 collects a fluid sample and electrochemically analyzes the fluid sample using electrodes, as is known in the art. A current response is measured that is indicative of the concentration of an analyte in the fluid. The test strip 104 is any strip capable of testing a fluid sample and transmitting the results to the metering device 102. In one embodiment, the test strip 104 includes technology that allows radio frequency identification (RFID) tags to be created on materials including paper having conductive non-metallic ink.

RFID technologies can exhibit several different opposing characteristics: electric field (capacitive) vs. magnetic field (inductive); passive vs. active; near field vs. very-near field; near field vs. far field (BlueTooth, WiFi, etc.). The present invention contemplates the use of any of these RFID technologies for the purpose of moving measurement and other data from the test strip 104 to the meter 102.

Two considerations for the appropriate type of RFID communication for any test strip 104 design are range (distance) and power. For example, communication via inductive coupling (magnetic field) is good for relatively longer distances, but requires a relatively great deal of power. In contrast, communication via capacitive coupling (electric field) has good power efficiency, but distance is limited. Similarly, passive RFID communication requires less power (including no power required on the test strip itself) but can only be used over shorter distances, in contrast to active RFID communication that requires more power (including a power source on the test strip itself) but can cover longer distances.

The test strips 104 disclosed and claimed herein can be configured with many different types of RFID tags. The meter 102 can be configured with an RFID reader which sends a signal to the RFID tag when the test strip 104 is brought within close proximity of the meter 102. The meter 102 can thus receive the data that is stored on the RFID tag.

As described in greater detail hereinbelow, in one example of an RFID system suitable for use in embodiments of the present invention, the RFID reader includes a transceiver and an antenna that emits electromagnetic radio signals to activate the RFID tag, which includes its own transceiver and antenna. Interrogation signals from the reader activate the tag, causing the tag to send a return signal including the information encoded on the tag.

In some embodiments, the RFID system can operate via a technique known as continuous wave backscatter. In this technique, the reader transmits a continuous-wave interrogation signal to the tag, and the tag modulates the continuous wave interrogation signal to produce a backscatter response signal that is transmitted back to the reader. This backscatter response signal includes the information encoded on the tag, such as the lot number, expiration date, calibration data, measurement data or other information concerning the test strips.

A variety of suitable RFID tag systems are commercially available. Presently, there are three main categories of commercially available RFID systems. There are systems that employ beam-powered passive tags, battery-powered semi-passive tags, and active tags. A beam-powered RFID tag is often referred to as a passive device, in that it derives the energy needed for its operation from the radio frequency energy beamed at it (from the reader). Such a passive tag rectifies the field and changes the reflective characteristics of the tag itself, creating a change in reflectivity (RF cross-section) that is then seen at the reader. A battery-powered semi-passive RFID tag operates in a similar fashion, modulating its RF cross-section in order to change its reflectivity that is seen at the interrogator to develop a communication link. However, the semi-passive RFID tag has a battery to provide the tag's operational power. Finally, in the active RFID tag, both the tag and reader have transceivers to communicate and are each powered by their own batteries.

The range of communication for RFID tags in general depends upon the transmission power of the reader and of the tag, with a greater range requiring greater transmission power. RFID reader power for proper operation of passive RFID systems is a function of distance, antenna sizes, frequency, and orientation. Most RFID systems are intended for near-field applications. Distances between readers and tags are normally on the order of millimeters. An example of a simplified equation for inductive based passive devices that help illustrate the impact of distance changes is as follows:

$$H=(IN)/(2r(1+(d^2/r^2))^{1.5}$$

where H=magnetic field intensity, I=current through reader antenna coil, N=number of turns on the reader antenna coil, r=radius of the reader antenna coil, d=distance between the center of the reader antenna coil & the center of the tag antenna coil.

However, these equations are typically useful only when the d is of the same order of magnitude as r (i.e., near-field). Because a passive tag derives its power from the interrogation signal of the reader, the transmission power is dependent on the transmission power of the reader. To reduce the power demands on the reader and prolong the battery life of the reader, RFID systems used in the present invention can be configured to operate in a relatively short transmission range (on the order of inches), thus reducing transmission power requirements.

Limiting the RFID communications sessions to situations when the tag and reader are in close proximity further conserves battery life. For example, an RFID communication protocol may be employed that limits communications attempts from the reader (i.e. the sending of interrogations signals) to situations where a tag is present to be read. One such protocol places the reader in sleep mode until an activation switch is pressed on the meter. Pressing the activation switch activates the reader to send out its interrogation signal and to look for the response from the RFID tag. The response comes in a matter of milliseconds, and once the information from the RFID tag has been received at the meter, the reader goes back into battery conservation/sleep mode. Triggering the RFID tag interrogation signal based on the pressing of an activation switch serves to assure that communication is only attempted when the meter and the test strip are in sufficiently close proximity. In other embodiments, the reader may send out an interrogation signal continuously or intermittently, depending on the need to conserve power (e.g. the meter may be AC powered and can therefore send out a continuous interrogation signal).

As used herein, the term "transmitted" is intended to cover the movement of data between the test strip 104 and the meter 102 using any active or passive RFID technology, regardless of whether the data is being transmitted in the classic "active" sense, or whether it is otherwise being discerned, detected, interrogated, probed, or made available.

FIG. 1 illustrates and breaks down the metering device 102 and the test strip 104 each into four smaller components. These four smaller components are illustrated in the block diagram on the right side of FIG. 1. The metering device 102 includes a radio frequency identification (RFID) integrated circuit (IC) and antenna in block 110. Block 110 illustrates that the RFID IC and antenna can receive signals from the test strip 104. Also, block 110 illustrates that the metering device 102 in some embodiments transmits a signal to the test strip 104 to interrogate the test strip 104 for information and/or to power the test strip 104. Block 112 illustrates that the metering device 102 embodied in FIG. 1 is powered by replaceable long-life batteries. Alternatively, in other embodiments the metering device 102 is powered by an AC power source, rechargeable batteries, or any other power source as will be apparent to those skilled in the art. The metering device 102 also includes a microprocessor in block 114. The microprocessor of block 114 has computational circuitry to analyze the signal received from the test strip 104. In some embodiments, a firmware algorithm is used to calculate the concentration of glucose in a fluid sample from the signals received from the test strip 104. In addition, in some embodiments, the microprocessor of block 114 includes circuitry to convert the data information into a read-out on the display screen 106 that is readable by the user of the metering device 102. In addition, in many embodiments, the microprocessor of block 114 includes an analog to digital converter. The metering device 102 also includes the block 116 indicating that the device has a display 106 and buttons 108 as described hereinabove.

FIG. 1 also illustrates one embodiment of the test strip 104 broken down into four different components. First, in block 118, the test strip 104 has a radio frequency identification integrated circuit (RFID IC) and an antenna. The circuit transmits information to the meter 102 about the current response sensed in the tested fluid sample. Also, in some embodiments, it is the part of the test strip 104 that receives a signal from the metering device 102. The test strip 104 also includes in some embodiments, such as the illustrated embodiment, a thin film battery in block 120. The thin film battery of block 120 powers the test strip 104. In some embodiments, the test strip 104 does not include a battery 120, but instead uses an antenna to couple electromagnetic energy transmitted by the meter 102 and this energy is used to power the test. For example, the meter 102 may generate a signal of approximately 100 kHz that is received by an antenna on the test strip and this energy is used to excite the sample fluid on the test strip and power the circuitry on the test strip 104.

In embodiments wherein the information is transmitted to the metering device 102 as a digital signal, the test strip 104 also includes an analog-to-digital converter in block 122 of the illustrated embodiment. In some embodiments, the circuit includes a clock. In other embodiments, a clock signal is provided by the metering device 102. The analog-to-digital converter converts the current/voltage response obtained by the electrodes into a pattern of binary bits that can be easily transmitted by the RFID IC circuit by modulating a radio frequency signal, as is known in the art. The test strip 104 also includes a drop detect/current-to-voltage circuit in block 124. The drop detect circuit of block 124 closes a switch in response to a sufficient change in response detected between the measurement electrodes. As a result, when a fluid sample has been applied to the test strip, the current-to-voltage circuit 124 converts a current signal from the measurement electrode into a voltage signal, as is known in the art.

In operation, the remote measuring system 100 works as follows. First, a sample of blood is taken from the person to be tested and placed on the test strip 104. The drop detect/current-to-voltage circuit of block 124 first senses when sufficient blood sample is obtained. If the sample is acceptable, the drop detect/current-to-voltage circuit of block 124 converts the electrochemically-induced current flowing through the fluid sample and measured using the measurement electrodes into a proportional voltage, as is known in the art. After successful drop detection, this voltage is converted by the analog-to-digital converter in block 122 into a series of binary bits of information. These bits of information are sent to block 118 containing the RFID IC and antenna. The RFID IC of block 118 formats the received information and produces a modulated signal, which is broadcast via an antenna to the metering device 102. The modulated signal is sensed by the metering device 102. The RFID IC and antenna in block 110 of the metering device 102 receives these signals and demodulates them into binary bits, which are then sent to the microprocessor in block 114. The microprocessor in block 114 receives the binary bits and uses computational circuitry, such as firmware algorithms, to determine the validity of the signals and concentration of the indicated analyte. Once this concentration is determined, an output signal of any relevant or desirable information is sent from the microprocessor of block 114 to the user interface display 106. In addition, the buttons 108 may control different functions of microprocessor in block 114 to manipulate the data received, or adjust the sequence of testing. The microprocessor of block 114 is controlled by an operating algorithm having a mathematical relationship between the concentration of the analyte to be tested and the current data encoded with the binary bits. The display 106 informs the treating physician, health professional, or other user of the concentration of the analyte to be measured, such as glucose. Because it is not necessary to insert the test strip 104 into the meter 102 in order to conduct a test, the system 100 improves sanitation and robustness, and greatly reduces the level of dexterity required to administer the test strip 104.

The test meters and sensors disclosed herein can be configured in many different embodiments that are generally driven by a balance between cost and quality. In a lower cost (lower quality) embodiment, there is a minimum of electronics on the test strip 104 itself, such that power and the clocking signal are provided by the metering device 102 and analog data is streamed to the meter 102 in real time. One disadvantage of this embodiment is that a broken stream of data (caused, e.g., by moving the test strip 104 too far from the metering device 102 for proper reception) will make the test fail. There are various possible upgrades to this lower cost embodiment, such as adding an analog-to-digital converter onto the test strip 104 so that the streaming data is digital, or adding a self-contained clock to the test strip 104. Nevertheless, this embodiment provides a low-cost option by keeping the test strip 104 relatively simple.

In a highest quality (higher cost) embodiment, the test strip 104 has power, clock, A/D converter, and digital storage on the strip. The data does not need to be streamed in real time from the test strip 104 to the meter 102, but rather be stored until the test strip 104 can verify an available interface with a meter 102, e.g., before making the data available to be read.

In a third embodiment, the electronics of the metering device 102 and test strip 104 are relatively simple and minimal, wherein an intermediate device is provided that contains much of the remaining system requirements. An example of an intermediate device is a fob, watch, or pen device that can be easily carried by the user. In a first species of this third embodiment, the intermediate device serves as a data carrier, wherein much of the system electronics are moved to the intermediate device from the metering device 102 and the test strip 104, such that the intermediate device acts as a data "weigh-station" between the meter 102 and the test strip 104. In use, only the test strip 104 and the intermediate device, e.g. a fob, would need to be in proximity to each other during the test, and the fob would later interact with the metering device 102 for purposes of transferring the relevant information and displaying a result. The fob can optionally hold test data from more than one test.

In a second species of the third embodiment, the metering device 102 is provided in a carrier that serves as an electrical-systems hub, such that the intermediate device can be placed or plugged into the carrier when convenient and the measurement then takes place once the data is transferred from the intermediate device to the carrier metering device 102. In some embodiments, the carrier is essentially the meter 102 that is designed to mate with the intermediate device, having a display, buttons, etc. In other embodiments, the carrier is simply a hub/interface between the meter 102 and intermediate device, e.g. a docking station.

This third embodiment is useful, for example, in a hospital setting, in which the diagnostic technician takes glucose measurements of more than one patient. Rather than carrying around the meter and subjecting it to possible contamination from the various fluid samples, the technician needs only to apply the fluid sample to a test strip 104 that is in proximity to an intermediate device, such as a fob carried on the technician's person. The test strip 104 is discarded after the test sequence, and the intermediate device is subsequently returned to the vicinity of the metering device 102 for purposes of downloading the measurement information.

Figure 2:
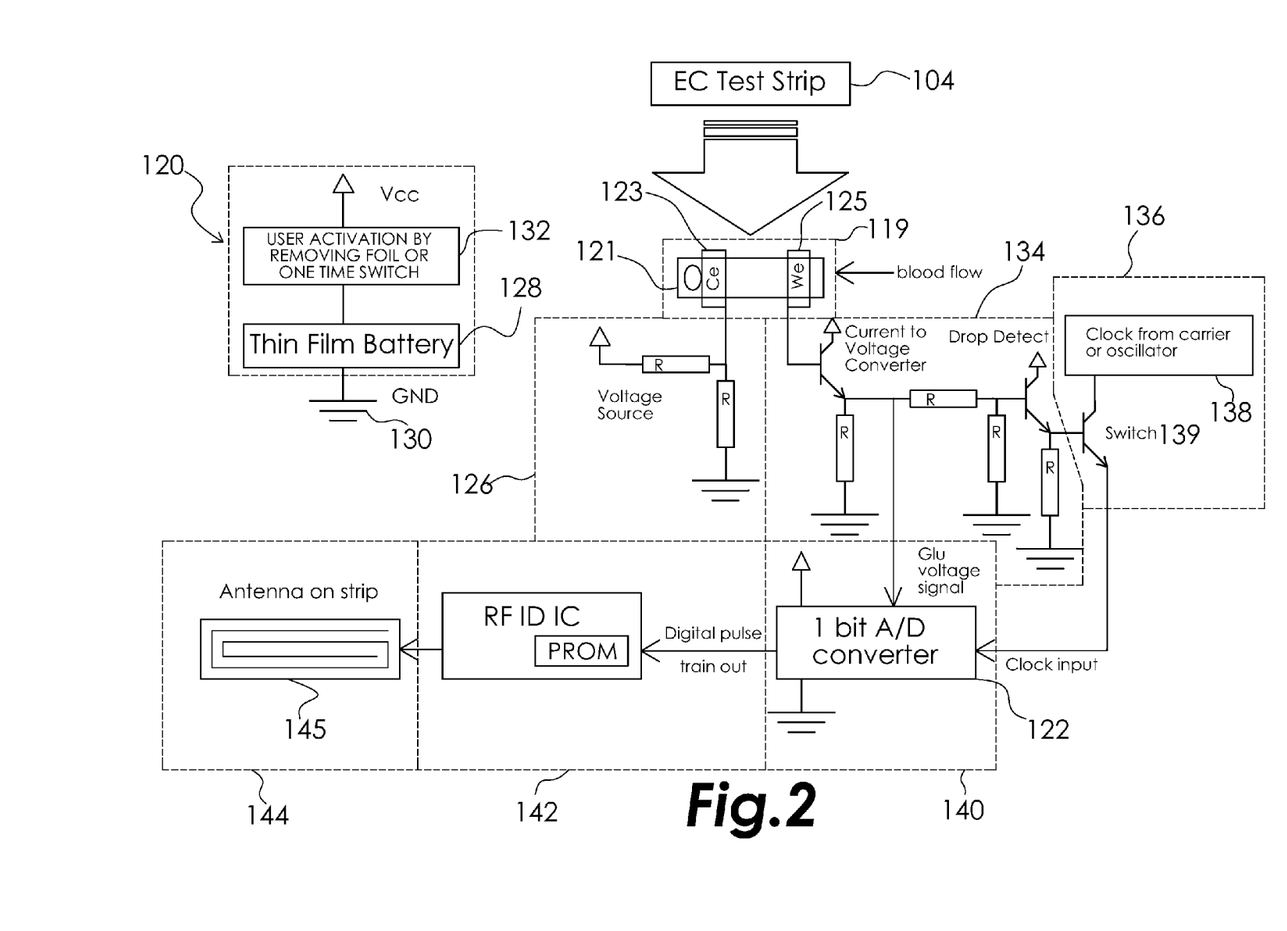
FIG. 2 is a schematic illustration of one configuration of a test strip according to the embodiment illustrated in FIG. 1.

FIG. 2 illustrates in more detail one test strip 104 according to the embodiment illustrated in FIG. 1. The test strip 104 comprises seven main sections. The first section, the reaction zone 119, is where an electrochemical reaction using the fluid sample is performed, as is known in the art. Powering section 126 provides an excitation stimulus to the electrodes in the reaction zone. The next section, the conversion section 134 converts the current produced in the measurement zone 119 to a voltage signal. The timing section 136 couples a clock 138 to section 140 to drive the analog-to-digital converter after sufficient sample is detected. The section 140 comprises the analog-to-digital converter that receives the voltage signal from the conversion section 134 and the timing signal from the timing section 136. The section 140 uses these two input signals to form a digital pulse train representation of the voltage produced by the conversion section 134 that can be easily represented by a modulated radio frequency signal. The section 142 corresponds to the RFID IC. The section 144 includes the antenna 145 that conveys a signal to be gathered by metering device 102.

The reaction zone at 119 includes three main components. The first component is the fluid sample 121. In many embodiments, the fluid is blood and the analyte to be determined is glucose, however, those skilled in the art will recognize that many different types of fluids and analytes can be analyzed using the system disclosed herein. The reaction zone 119 also includes a counter electrode 123 and a working electrode 125. In some embodiments, the reaction zone includes a vented capillary space which draws the fluid sample 121 toward the capillary vent when the fluid sample 121 is presented at the other end of the capillary. The traversal of the capillary draws the fluid sample 121 over the electrodes 123, 125. In some embodiments, the electrodes are covered with a reagent to create a chemical reaction in the fluid sample to be tested. In addition, the electrodes 123, 125 are comprised of a conductive material such as a metal, conductive ink, or other types of conductive material readily apparent to those skilled in the art. When a fluid sample 121 has been placed into the reaction zone 119, it reacts with the reagent that is placed upon the counter and working electrodes 123, 125. This chemical reaction changes the impedance sensed across the electrodes 123, 125. This impedance change is measured to determine the concentration of different analytes in the fluid sample 121.

A potential is created in the reaction zone 119 using a voltage source from the powering section 126. The voltage source includes a thin film battery 128 in some embodiments. Other embodiments do not have a thin film battery because all power is remotely provided by a signal sent from the metering device 102. Alternative embodiments use other power sources. The thin film battery 128 is attached to the ground 130 on one side as illustrated in FIG. 2. The block 132 is a device for activation of the thin film battery 128. In some embodiments, removing a foil that surrounds the thin film battery 128 activates the battery which was previously inactive in order to conserve the energy stored therein. In addition, in some other embodiments, the thin film battery 128 can be activated using a one time switch. The thin film battery 128 sometimes provides only a minimal amount of power. The metering device 102 provides the remainder of the power to operate the circuitry in some embodiments, as discussed hereinabove. It is contemplated, in other embodiments, however, that all energy needs can be provided from the thin film battery 128. In the embodiment of FIG. 2, the battery 128 voltage is decreased in a voltage divider network as illustrated in powering section 126 prior to being applied to the counter electrode 123.

The reaction of the fluid sample 121 with the reagent causes a current to flow to electrode 125 that is coupled to the conversion section 134. The conversion section 134 transforms the current signal to a voltage signal using a current-to-voltage converter circuit, as is known in the art. In addition, in some embodiments, the conversion section 134 includes a drop detect circuit as shown in FIG. 2 that functions to couple clock 138 to the analog-to-digital converter 122 in order to provide a timing signal for the conversion. When sufficient current is detected at the working electrode 125 and converted to a voltage by the current-to-voltage circuit, this voltage turns on transistor switch 139, thereby coupling the clock 138 to the analog-to-digital converter 122. Because no current will appear at the working electrode until the fluid sample 121 covers both of the electrodes 123, 125 (i.e. the "drop detect" function), and because the analog-to-digital converter 122 is not activated until a current is detected at the working electrode 125, the test strip 104 saves power until there is a drop detect of the fluid sample 121 and there is a current ready to be measured and transmitted to the meter 102.

The analog-to-digital converter 140 receives as input the voltage provided by the conversion section 134 and the clock signal from the timing section 136 and converts the voltage into a digital pulse train. The digital pulse train is sent out from the analog-to-digital converter section 140 to section 142 that includes the RFID IC.

The RFID IC of section 142 receives the digital pulse train provided by the analog-to-digital converter and turns it into a complementary radio frequency signal that can be modulated to represent the digital data received.

The RFID IC circuit also includes antenna in section 144 that acts as a coil to allow the transmission of data to the metering device 102 by modulating the amplitude of the electromagnetic field. In addition, in some embodiments, the antenna 144 can receive signals from the metering device 102 in a similar manner. In select embodiments, the antenna is constructed of a metal material. In other embodiments, the antenna is formed from technology similar to the BiStatix™ technology from Motorola® that uses a non-metallic conductive ink printed on paper to lessen costs and to improve durability.

The test strip 104 illustrated in FIG. 2 operates as follows. A fluid sample 121 is obtained from the user and placed across the electrodes 123 and 125. A stimulation voltage is applied to the fluid sample using the potential that exists in thin film battery 128 of the powering section 126. Additionally, in some embodiments, the metering device 102 provides a portion or all of the stimulation voltage by coupling electromagnetic energy through the antenna 145. The current is generated in the fluid sample 120. The initial generation of current through the sample is detected by the drop detect circuitry and indicates that the size of the sample is appropriate for measurement. Next, the reagent placed upon the electrodes 123 and 125 induces a chemical reaction in the fluid sample 120. The chemical reaction alters the conductivity of the fluid sample and results in a change in impedance across the sample. This impedance change is reflected in the altered current sensed by the conversion section 134, where the current is converted into a corresponding voltage signal using current-to-voltage conversion circuitry, as is known in the art. The voltage signal is relayed to the analog-to-digital converter 122 in section 140. In addition, a clock 138 in timing section 136 sends a timing signal to the analog-to-digital converter 122 in section 140 after activation of the switch 139 by drop detect circuitry. The analog-to-digital converter 122 uses this timing signal during its conversion of the voltage signal from conversion section 134 to a digital signal. The RFID IC receives this digital signal in section 142. The RFID IC transforms the digital signal into modulated radio frequency signals that are transmitted to the metering device 102 by the antenna in section 144. Thus, the test strip 104 essentially begins with an electro-chemically induced impedance change in a fluid sample and transforms it into a modulated radio frequency signal capable of transmitting impedance or current data to the meter 102. In other embodiments, however, radio frequency is not used and other types of communication methods are used. For example, infrared, laser, ultrasonic, and other electromagnetic wavelength carrier signals are used.

It should be noted that in some embodiments the test strip 104 sends a signal to be received by the metering device 102, however, in other embodiments, both the test strip 104 and the metering device 102 transfer signals back and forth. For example, in some embodiments, the metering device 102 may send a signal that provides the power in order to operate the circuitry on the test strip 104. In other embodiments, the metering device 102 sends only modulated data, a password, or some combination of one or more types of data and/or the operating power. The signal in the illustrated embodiments is radio frequency, however, alternate forms of transmitting information are contemplated by other embodiments.

Figure 3:
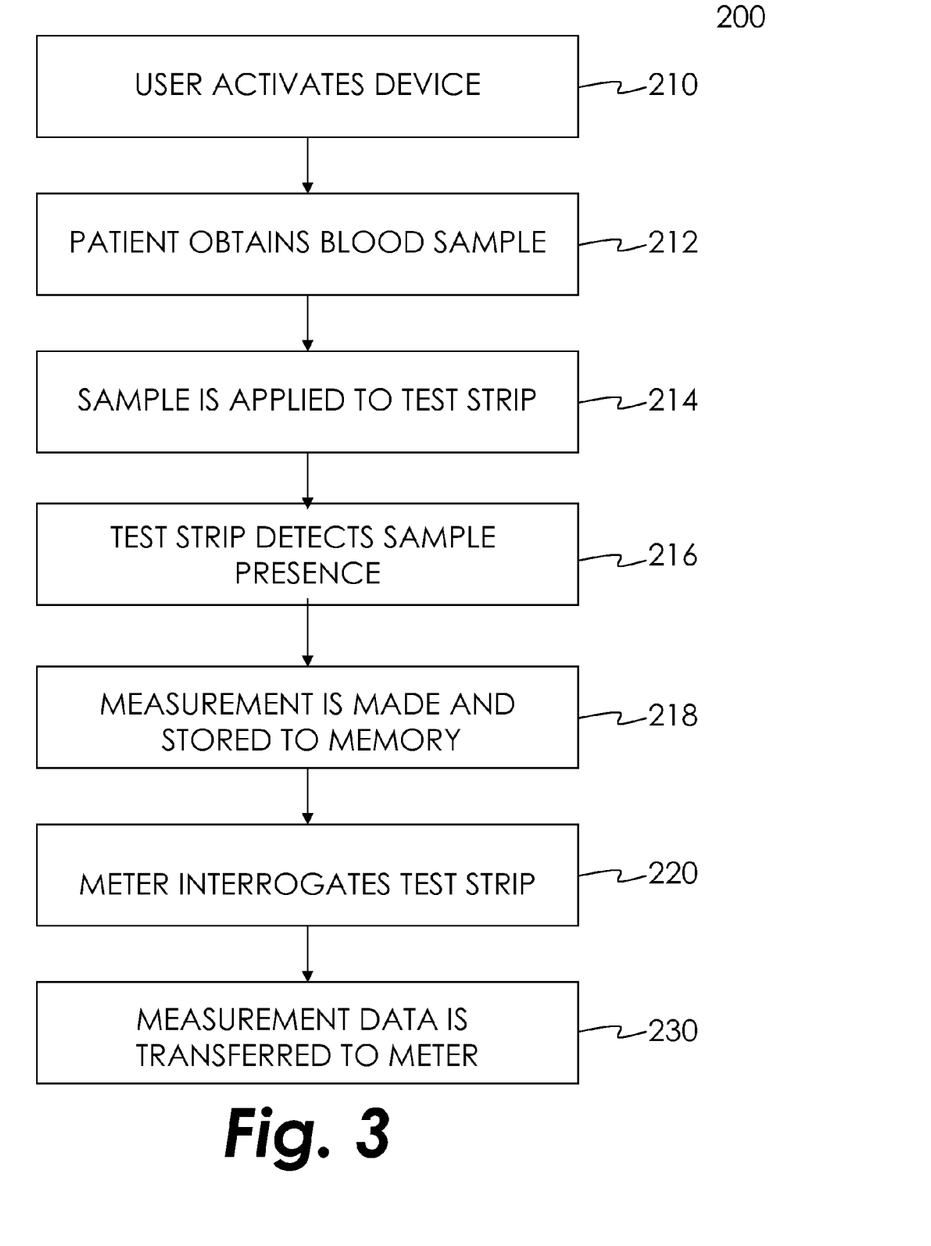
FIG. 3 is a flow diagram illustrating the use of a test strip according to the embodiments illustrated in FIGS. 1 and 2.

FIG. 3 is a flow diagram outlining the use of an embodiment of test strip 104 with continuing reference to the embodiments illustrated in FIGS. 1 and 2. At step 210, the user activates test strip device 104. In at least one embodiment, the user activates test strip 104 by removing a foil covering a thin film battery 128 or actuating a one-time switch 132, which causes thin film battery 128 to provide power to a drop detect/current-to-voltage circuit in block 124, a one bit A/D converter with optional clock and RFID IC & antenna block 118. System 200 proceeds to step 212.

At step 212, the patient obtains a fluid sample 121 to be tested. In some embodiments, the fluid is blood, and the analyte to be determined is glucose. However, it will be understood by those skilled in the arts that different qualities and types of fluids could be analyzed using the system of the present embodiment. System 200 proceeds to step 214.

At step 214, a fluid sample 121 is applied to the reaction zone 119 of test strip 104. When fluid sample 121 is placed into the reaction zone 119, it reacts with a reagent. The chemical reaction causes a change in the electrical properties of the reaction zone 119 across the counter and working electrodes 123, 125. System 200 proceeds to step 216.

At step 216, drop detect circuit with I/V 124 detects the presence of the sample in the reaction zone 119 of test strip 104. The drop detect/current-to-voltage circuit of block 124 converts the electrochemically-induced current across the fluid sample as measured using the measurement electrodes 123 and 125. If the sample dosage is acceptable, a voltage is detected across the measurement electrodes, which is converted by the analog-to-digital converter 122 into a series of binary bits containing measurement information. System 200 then proceeds to step 218.

At step 218, test strip 104 measures the change in electrical properties in the reaction zone 119 and stores the information in memory. In some embodiments, a change in impedance is measured across the electrodes 123, 125 to given an indication of the concentration of different analytes in the fluid sample 121. In other embodiments, a current is measured, wherein the chemical reaction of the sample under test 119 and the reagent in reaction zone 119 causes a current to flow between electrodes 123, 125. The measured current provides an indication of the concentration of an analyte of interest in the fluid sample 121. The one bit A/D converter 122 samples the voltage signal provided by the current to the voltage converter of block 134. A digital pulse train is provided to the RFID IC block 142, which stores the collected data in memory. System 200 proceeds to step 220.

At step 220, test meter 102 interrogates test strip 104 via an RFID carrier and receives the carrier and signal from test strip 104. In some embodiments, the user initiates a search algorithm by test meter 102 to seek out a test strip 104 in near proximity to the meter 102. In other embodiments, test meter 102 detects automatically the presence of test strip 104 after test strip 104 is activated. Illustratively, as a non-limiting example, test meter 102 periodically transmits an RFID carrier seeking to detect a passive RFID receiver contained in test strip 104. The test strip 104 will respond to the test meter 102 after completion of the user activation step 210. It will be understood that the above described detection techniques are illustrative and that other methods of detecting the presence of a test strip, either activated or non-activated, within a desired region proximate to meter 102 are contemplated by the various embodiments of the present invention. After detecting the presence of the test strip, system 200 goes to step 230.

At step 230, test strip 104 transfers the stored measurement data to meter 102. In at least one embodiment, the RFID IC formats the data and produces a modulated signal, which is broadcast via an antenna to the metering device 102. The modulated signal is sensed by metering device 102, which demodulates the signal to recover the measurement data. Microprocessor 114 receives the binary bits and uses computational circuitry, as described above, to determine the validity of the measured signals and determine the concentration of the analyte of interest in fluid sample 121.

In at least one alternative embodiment, the test strip is activated upon being dispensed from a dispenser unit holding at least one test strip. In an alternative embodiment, a test strip is activated upon receiving an RFID activation signal from meter 102. Upon activation, the test strip automatically undergoes a calibration step according to various methods. It will also be understood that in addition to providing measurement data, the RFID link embedded in the test strip can also communicate calibration information from test strip 104 to the meter 102. In addition, in an alternative embodiment, a test strip dispenser having a passive or active RFID circuit provides calibration data upon interrogation by meter 102.

Moreover, in still other embodiments, test strip 104 interactively operates with test meter 102 to ensure that a sufficient dosage of a sample fluid 121 is deposited in the reaction zone 119 of test strip 104. As a non-limiting example, upon activation, meter 102 interrogates test strip 104 to determine whether a sufficient sample dosage 121 is deposited in reaction zone 119. If an insufficient dosage is present, an indication is sent to meter 102, which then displays a message "insufficient dosage" on user interface display 106. User interface display 106 instructs the user to continue applying additional fluid sample 121 to test strip 104. After the drop detect circuit 124 detects that there is a sufficient sample size to allow test strip 104 to provide accurate data, test strip 104 provides an indication via the RFID link to meter 102 that a sufficient sample was deposited within reaction zone 119. Upon receiving the indication from the RFID IC 142, either through active interrogation by test meter 102 or an RFID transmission signal from test strip 104, test meter 102 displays the message "sufficient dose applied" on test meter display 106. As another non-limiting example, test meter 102 includes at least one LED to provide an indication to the user that a sufficient dosage has been provided to allow for an accurate test. Illustratively, a single diode device having both a red and green output may be used to signal the user to provide additional sample volume. When the device 102 shows the color green, a sufficient dosage is present in reaction zone 119; however, when the illumination is red, an insufficient dosage is present in reaction zone 119. Alternatively, a two diode system may be used, wherein the first LED is illuminated to indicate an insufficient dosage while a second LED is used to indicate a sufficient dosage is present.

It will be understood that in still other embodiments the time period between initial dispensing of the test strip 104, the activation of the test strip 104 by the user, or the detection of sample application onto the test strip 104 and the application of a sufficient dose of fluid sample 121 may be reported to test meter 102 by test strip 102. Test meter 102 can then determine whether the passage of time adversely affects the measurement data reported by test strip 104. As a non-limiting example, either test meter 102 or test strip 104 can calculate the period of time between an initial application of a fluid sample 121 and dose sufficiency. If the passage of time would cause test strip 104 to provide an inaccurate measurement, test meter 102 can provide an indication to the user that the test strip data is not valid along with an appropriate correctional instructions.

Several embodiments have been described herein of a body fluid testing system that provides a convenient and fast way to test for the presence of an analyte using test strips that can be dosed without having to be inserted into a metering device (i.e. out-of-meter dosing) either before or after dosing. The test strips are therefore very easy to handle because the meter does not have to be held or otherwise manipulated during the test, and the fluid sample does not have to be subsequently brought into contact with the meter. Additionally, the test meter may be configured so as to lack the test strip connector (and its associated opening) found on prior art body fluid test meters. Thus, the robustness of the meter is enhanced because it stays clean, avoids contamination of subsequent samples, and without the need for a test strip port or other opening, it can be designed to be sealed to outside contaminants such as dirt and moisture that may otherwise affect a measurement result or the robustness of the meter. In some embodiments, the meter case is completely sealed and waterproof or water resistant.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A disposable test element comprising: an electrochemical biosensor adapted to react a sample of a patient's blood with one or more reagents and to sense an electrical characteristic of the sample during the reaction with the disposable test element not being connected to any metering device, and circuitry operable to receive a wireless input signal from a remote monitor, the wireless input signal including clocking information, the circuitry further operable to utilize the clocking information from the wireless signal in combination with a circuit including the sample to provide clocked output of information indicative of a patient's blood glucose and sample quantity information, and provide a wireless signal including the clocked output receivable by the remote monitor with the disposable test element not being connected to any metering device.

2. A method comprising:
providing a sample of biological fluid to a disposable biosensor;
reacting the sample with a reagent in the biosensor;
sensing a current characteristic of the sample during the reacting;
receiving a wireless input signal from a remote monitor, the wireless input signal including timing information;
utilizing the timing information to provide output including sample characteristic information and sample quantity information;
outputting a wireless output signal including the timed output receivable by the remote monitor;
receiving and storing the output information at the remote monitor;
transferring the received and stored information from the remote monitor to a processing unit; and
determining blood glucose information at the remote monitor or the processing unit or both;
wherein said acts of providing, reacting, sensing, receiving, utilizing, and outputting occur with the disposable biosensor not being physically connected to a metering device.

3. A system comprising: a metering device, an in vitro test strip, and a remote intermediate device, the remote intermediate device comprising circuitry operable to wirelessly send and receive signals to and from the test strip; the test strip comprising circuitry operable to wirelessly send and receive signals to and from the remote intermediate device and a reaction zone for receiving a fluid sample and performing an electrochemical reaction; wherein the test strip is configured to apply a potential to the reaction zone when a sample is received in the reaction zone, to obtain an electrochemical response of the reaction zone to the potential, and to generate and transmit a first signal corresponding to the electrochemical response to the remote intermediate device; and wherein the remote intermediate device is configured to receive the first signal from the test strip and provide said first signal to a processing circuitry configured to calculate a concentration of an analyte in the fluid sample based at least in part on said first signal, the processing circuitry being provided on one of the remote intermediate device and the metering device; the metering device comprising a display and circuitry operable to send and receive signals to and from the remote intermediate device, wherein the remote intermediate device is configured to transfer to the metering device one or both of the first signal or second signals having information relating to the calculated concentration of the analyte, the metering device being configured to display the calculated concentration on the display.

4. The system according to claim 3 wherein the remote intermediate device is further configured to provide at least one of a clock signal, an activation signal, and a power signal to the test strip.

5. The system according to claim 3 wherein the response to the potential is a current response.

6. The system according to claim 3 wherein the remote intermediate device is a user-portable storage unit operable to store encoded information received from the test strip and further comprising a processing unit operable to receive the stored information from the user-portable storage unit and to process the information to provide information of a patient's blood glucose.

7. The system according to claim 3 wherein the test strip comprises a clock circuit or receives a clocking signal from the remote intermediate device, and the signal corresponding to the response of the reaction zone to the potential comprises a current response as a function of time.

8. The system according to claim 3 wherein the test strip is further configured to detect sufficient sample fluid application to the reaction zone.

9. The system according to claim 3 wherein the intermediate device is configured to receive a plurality of signals corresponding to respective electrochemical responses from a plurality of test strips and provide each of said plurality of signals to the processing circuitry to calculate a concentration of an analyte in the fluid sample from a particular one of said test strips, the metering device being configured to store each of the calculated concentrations.

10. The system of claim 9 wherein the metering device is configured to download a plurality of measurement information from the remote intermediate device.

11. The system of claim 3 wherein the intermediate device comprises one of a fob, a watch, and a pen device.

12. The system of claim 3 wherein the metering device comprises a carrier having a docking location configured to receive the remote intermediate device, the processing circuitry being provided on the carrier, wherein the remote intermediate device is configured to be plugged into the carrier and to transfer to the carrier a plurality of signals corresponding to respective electrochemical responses, the carrier transferring the plurality of signals to the processing circuitry for calculating analyte concentrations for a plurality of fluid samples.

13. A method comprising:
 (a) providing a sample fluid to a reaction zone of a test strip;
 (b) reacting the sample fluid with a reagent in the reaction zone;
 (c) applying a potential to the sample fluid in the reaction zone;
 (d) activating a clock for generating a timing signal corresponding to the potential;
 (e) measuring a current response of the sample during the reacting;
 (f) converting the current response and timing signal into an analog or digital signal;
 (g) wirelessly transmitting the analog or digital signal to a remote intermediate device;
 (h) providing the analog or digital signal to a processing circuitry configured to determine concentration of an analyte, the processing circuitry being provided on one of the remote intermediate device and a metering device;
 (i) using at least the analog or digital signal, determining the concentration of an analyte of the sample fluid; and
 (j) displaying the concentration on a display of the metering device.

14. The method according to claim 13 further comprising receiving and storing the analog or digital signal at the remote intermediate device.

15. The method according to claim 14 further comprising transferring the received and stored analog or digital signal to a processing unit.

16. The method according to claim 13 wherein the sample fluid is blood and the analyte is glucose.

17. The method according to claim 13 wherein the reagent includes glucose oxidase.

18. The method according to claim 13 wherein the analog or digital signal includes dosage sufficiency information.

19. The method according to claim 13 wherein the analog or digital signal includes Cottrell failsafe ratio information.

20. The method according to claim 13 wherein the analog or digital signal includes Cottrell current measurement information.

21. The method according to claim 13 wherein the processing circuitry is provided on the metering device, the metering device comprising a carrier having a docking location configured to receive the remote intermediate device, the method further comprising repeating steps (a) through (g) for a plurality of test strips and sample fluids, downloading from the intermediate device to the metering device the plurality of analog or digital signals, providing the plurality of analog or digital signals to the processing circuitry, and determining the concentration of an analyte of each of the plurality of sample fluids using at least the corresponding analog or digital signal.

* * * * *